(12) United States Patent
Oba et al.

(10) Patent No.: US 9,645,110 B2
(45) Date of Patent: May 9, 2017

(54) GAS SENSOR

(71) Applicant: NGK SPARK PLUG CO., LTD., Nagoya (JP)

(72) Inventors: Takehiro Oba, Konan (JP); Yuichi Yamada, Komaki (JP); Shingo Ito, Ichinomiya (JP); Makoto Kume, Inuyama (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 464 days.

(21) Appl. No.: 14/202,820

(22) Filed: Mar. 10, 2014

(65) Prior Publication Data
US 2014/0260531 A1    Sep. 18, 2014

(30) Foreign Application Priority Data

Mar. 13, 2013 (JP) .................................. 2013-050006
Jan. 8, 2014 (JP) .................................. 2014-001872

(51) Int. Cl.
*G01N 27/407* (2006.01)

(52) U.S. Cl.
CPC ................................ *G01N 27/4078* (2013.01)

(58) Field of Classification Search
CPC .................................................. G01N 27/4078
See application file for complete search history.

(56) References Cited

U.S. PATENT DOCUMENTS 4,169,778 A * 10/1979 Mann ................. G01N 27/4067
                                                                    204/429
4,970,898 A * 11/1990 Walish ................ G01L 19/0038
                                                                    73/706

(Continued)

FOREIGN PATENT DOCUMENTS

CN        102213691 A    10/2011
JP       2005-300185 A   10/2005

(Continued)

OTHER PUBLICATIONS

Office Action mailed Sep. 26, 2016 for the corresponding Chinese Patent Application No. 201410092682.3.

*Primary Examiner* — Laura Martin
*Assistant Examiner* — Alex Devito
(74) *Attorney, Agent, or Firm* — Leason Ellis LLP

(57) ABSTRACT

A gas sensor includes a sensor element having electrode take-out portions; a tubular separator having a flange portion, surrounding the electrode take-out portions, and spaced from a metallic shell; a tubular outer sleeve covering the separator, connected to the metallic shell, and having an inward convex portion that contacts the rearward-facing surface of the separator and restricts rearward movement of the separator; a seal member disposed on the rear of the separator and accommodated in a rear portion of the outer sleeve such that it is spaced from the separator; and an annular retainer fixed to the outer sleeve and in contact with a contact surface which forms at least a portion of the forward-facing surface of the flange portion. The separator has a rotation restriction surface for restricting its rotation in the circumferential direction, and the retainer has an engagement surface which contacts the rotation restriction surface.

10 Claims, 13 Drawing Sheets

(56) References Cited

U.S. PATENT DOCUMENTS

| | | | |
|---|---|---|---|
| 2004/0129566 A1* | 7/2004 | Nakagawa | G01N 27/4078 204/424 |
| 2007/0017193 A1 | 1/2007 | Nishio et al. | |
| 2010/0139379 A1* | 6/2010 | Kume | G01N 27/4062 73/114.73 |
| 2011/0239734 A1 | 10/2011 | Fujita et al. | |

FOREIGN PATENT DOCUMENTS

| | | |
|---|---|---|
| JP | 2006-153702 A | 6/2006 |
| JP | 2010-276452 A | 12/2010 |
| JP | 2011-133350 A | 7/2011 |

\* cited by examiner

GAS SENSOR

This application claims the benefit of Japanese Patent Applications No. 2013-050006 filed on Mar. 13, 2013 and No. 2014-001872 filed Jan. 8, 2014, all of which are incorporated by reference in their entirety herein.

FIELD OF THE INVENTION

The present invention relates to a gas sensor in which a rear end portion of a sensor element is accommodated in a separator and which detects the concentration of a specific gas component.

BACKGROUND OF THE INVENTION

Known examples of a gas sensor used for improving the fuel consumption of an internal combustion engine such as an automobile engine or for combustion control include an air-fuel-ratio sensor, and an oxygen sensor for detecting the oxygen concentration of exhaust gas.

Such a gas sensor generally has a structure in which a sensor element for detecting the concentration of a specific gas is held by a metallic shell, and electrode take-out portions (electrode pads) disposed on the surface of a rear end portion of the sensor element are surrounded by a tubular separator formed of ceramic. Terminal members attached to the separator are electrically connected to the respective electrode pads of the sensor element, a grommet (seal member) formed of rubber is disposed on the rear side of the separator, and the separator and the grommet are covered with an outer sleeve formed of metal. Lead wires are connected to the terminal members, and the lead wires are passed through through-holes of the grommet and are extended to the outside.

As a result of a rear end portion of the outer sleeve being crimped, the grommet is pressed toward the separator, whereby the separator is held between the grommet and a holding member located on the forward side of the separator.

Problems to be Solved by the Invention

However, if the rubber grommet deteriorates with age, the resilience of the grommet decreases, and its pressing force becomes weak, which may result in a decrease in separator holding force. In such a case, the friction between the separator and the grommet decreases, and the separator may rotate in the circumferential direction.

Also, since the separator receives the heat transmitted from the sensor element exposed to hot exhaust gas, the temperature of the separator becomes high. Therefore, if a structure in which the grommet presses the separator is employed, there arises a possibility that the heat of the separator is transmitted to the grommet, and the deterioration of the grommet is accelerated.

Also, in the case of the technique disclosed in Japanese Patent Application Laid-Open (kokai) No. 2010-276452, the separator is divided into forward and rear separators, and these separators are held by two holding members from the forward and rear sides thereof. However, the number of parts, including the separators and the retainers, increases.

Meanwhile, if an attempt is made to prevent transmission of heat by merely separating or spacing the grommet from the separator, the grommet becomes unable to hold the separator. Therefore, the separator may rotate in the circumferential direction, and may affect the connection between the terminal members and the electrode pads and/or damage the lead wires.

The present invention has been accomplished so as to solve the above-mentioned problems, and its object is to provide a gas sensor which suppresses thermal deterioration of a seal member and which can readily restrict rotation of a separator in the circumferential direction.

SUMMARY OF THE INVENTION

Means for Solving the Problems

First Configuration. In order to solve the above-described problems, the present invention provides a gas sensor comprising a sensor element extending in an axial direction and having a detection portion at a forward end thereof; a tubular metallic shell surrounding an outer circumferential surface of the sensor element; a tubular separator having a flange portion and surrounding the sensor element, the separator being spaced from the metallic shell; a tubular outer sleeve covering the separator and disposed on a rear side of the metallic shell, the outer sleeve having an inward convex portion which is in contact with a rearward-facing surface of the separator and restricts reward movement of the separator; a seal member disposed on a rear side of the separator and accommodated in a rear end portion of the outer sleeve such that the seal member is spaced from the separator; and an annular retainer fixed to the outer sleeve and being in contact with a contact surface forming at least a portion of a forward-facing surface of the flange portion, wherein the separator has a rotation restriction surface which restricts rotation of the separator in a circumferential direction, and the retainer has an engagement surface which comes into contact with the rotation restriction surface.

According to this gas sensor, it is possible to separate the seal member from the separator to thereby suppress thermal deterioration of the seal member. Also, instead of the seal member, the inward convex portion of the outer sleeve comes into contact with the rearward-facing surface of the separator to thereby restrict rearward movement of the separator. Therefore, the separator can be held between the retainer and the inward convex portion easily and reliably. Moreover, rotation of the separator in the circumferential direction, which would otherwise occur due to separation of the seal member from the separator, can be readily restricted by providing the engagement surface and the rotation restriction surface on the retainer and the separator, respectively, without providing a separate member for rotation restriction.

Second Configuration. The gas sensor of the first configuration may be configured such that a plurality of the contact surfaces are formed on the forward-facing surface of the flange portion at predetermined intervals in the circumferential direction; and the rotation restriction surface is formed between adjacent ones of the contact surfaces.

According to this gas sensor, the engagement between the engagement surface and the rotation restriction surface occurs at a plurality of positions in the circumferential direction. Therefore, rotation of the separator in the circumferential direction can be restricted more reliably.

Third Configuration. The gas sensor of the first configuration may further comprise an inner sleeve which is disposed inside the outer sleeve and which has a tubular portion extending in the axial direction and an extension portion extending radially inward from the tubular portion, a forward-facing surface of the inner sleeve being in contact with the rearward-facing surface of the separator, wherein a forward-facing surface of the seal member is in contact with the extension portion of the inner sleeve.

According to this gas sensor, the inner sleeve is disposed between the seal member and the separator; however, the contact area between the inner sleeve and the separator is small. Therefore, transmission of heat from the separator to the seal member decreases, whereby thermal deterioration of the seal member can be suppressed. Also, since the separator is pressed forward by the seal member via the inner sleeve, the separator can be held between the retainer and the inner sleeve easily and reliably.

Fourth Configuration. Also, the present invention provides a gas sensor comprising a sensor element having a detection portion at a forward end thereof; a tubular metallic shell surrounding an outer circumferential surface of the sensor element; a tubular separator having a flange portion and surrounding the sensor element, the separator being spaced from the metallic shell; a tubular outer sleeve covering the separator and disposed on a rear side of the metallic shell; an inner sleeve disposed inside the outer sleeve and having a tubular portion extending in the axial direction and an extension portion extending radially inward from the tubular portion, a forward-facing surface of the inner sleeve being in contact with the rearward-facing surface of the separator; a seal member having a forward-facing surface in contact with the extension portion of the inner sleeve and accommodated in a rear end portion of the outer sleeve such that the seal member is spaced from the separator; and an annular retainer fixed to the outer sleeve and being in contact with a contact surface forming at least a portion of a forward-facing surface of the flange portion, wherein the separator has a rotation restriction surface which restricts rotation of the separator in a circumferential direction, and the inner sleeve has an engagement surface which comes into contact with the rotation restriction surface.

According to this gas sensor, the inner sleeve is disposed between the seal member and the separator; however, the contact area between the inner sleeve and the separator is small. Therefore, transmission of heat from the separator to the seal member decreases, whereby thermal deterioration of the seal member can be suppressed. Also, since the separator is pressed forward by the seal member via the inner sleeve to thereby restrict rearward movement of the spacer, the separator can be held between the retainer and the inner sleeve easily and reliably. Furthermore, rotation of the separator in the circumferential direction, which would otherwise occur due to separation of the seal member from the separator, can be readily restricted by providing the engagement surface and the rotation restriction surface on the inner sleeve and the separator, respectively, without providing a separate member for rotation restriction.

Fifth Configuration. The gas sensor of the fourth configuration may be configured such that a plurality of the contact surfaces are formed on the rearward-facing surface of the separator at predetermined intervals in the circumferential direction; and the rotation restriction surface is formed between adjacent ones of the contact surfaces.

According to this gas sensor, the engagement between the engagement surface and the rotation restriction surface occurs at a plurality of positions in the circumferential direction. Therefore, rotation of the separator in the circumferential direction can be restricted more reliably.

Sixth Configuration. In the gas sensor of the present invention, the seal member may have a gas passage hole extending therethrough in the axial direction, and a water-repellent gas passage filter may be inserted into the gas passage hole, the gas passage filter having a forward-facing surface in contact with the extension portion of the inner sleeve.

Seventh Configuration. Also, the extension portion of the inner sleeve may have a through-hole which communicates with the gas passage hole, a tubular filter retainer may be further inserted into the gas passage hole, and a forward-facing surface of the filter retainer may be in contact with the extension portion of the inner sleeve in a state in which the through-hole communicates with an internal space of the filter retainer.

Eighth Configuration. The gas passage filter may be a sheet filter which covers an outer surface of the filter retainer, the filter retainer may have a collar portion which projects radially outward from a forward end of the filter retainer, and a forward-facing surface of the collar portion may be in contact with the extension portion of the inner sleeve.

According to this gas sensor, in the case where a reference gas (atmosphere) is introduced from the outside into the gas sensor via the gas passage filter within the seal member, forward coming off of the gas passage filter and the filter retainer disposed in the seal member can be prevented by bringing the extension portion of the inner sleeve into contact with the gas passage filter, the filter retainer, and the forward-facing surface of the collar portion thereof.

Effects of the Invention

According to the present invention, it is possible to suppress thermal deterioration of the seal member of the gas sensor and to readily restrict rotation of the separator in the circumferential direction.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Embodiments of the present invention will next be described.

Figure 1:
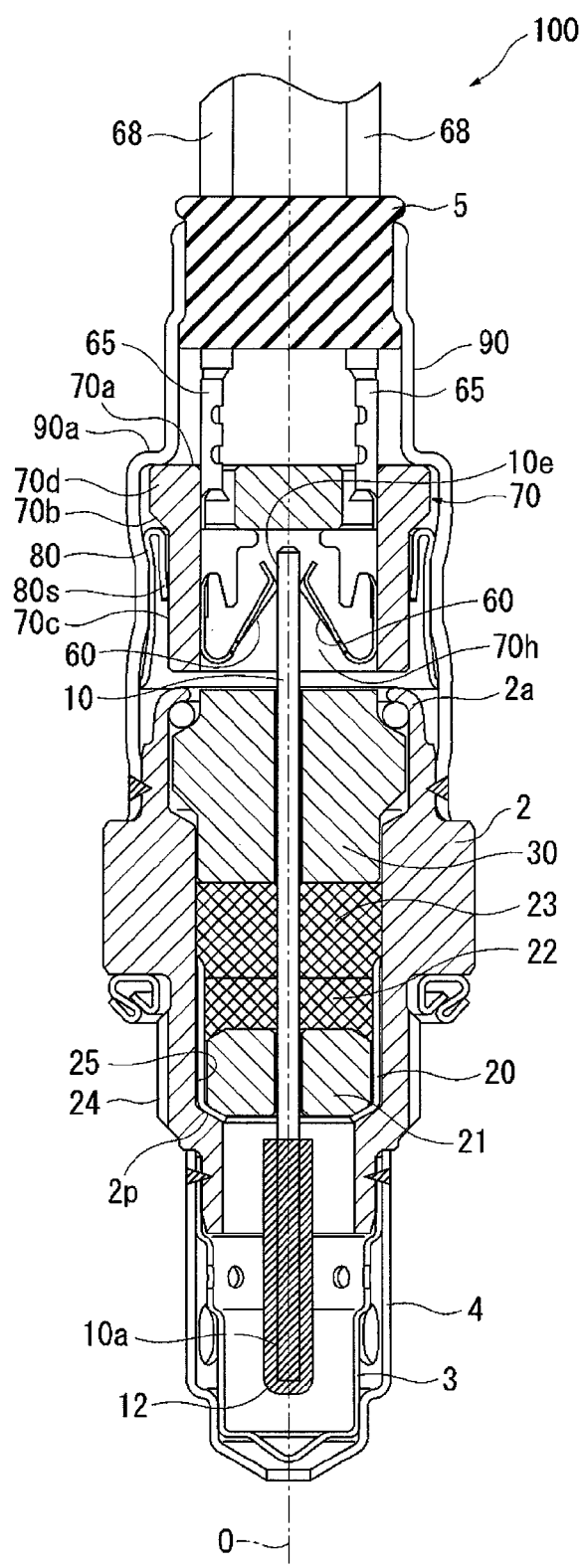
FIG. 1 is a cross-sectional view of a gas sensor according to a first embodiment of the present invention taken along the axial direction thereof.
Figure 2:
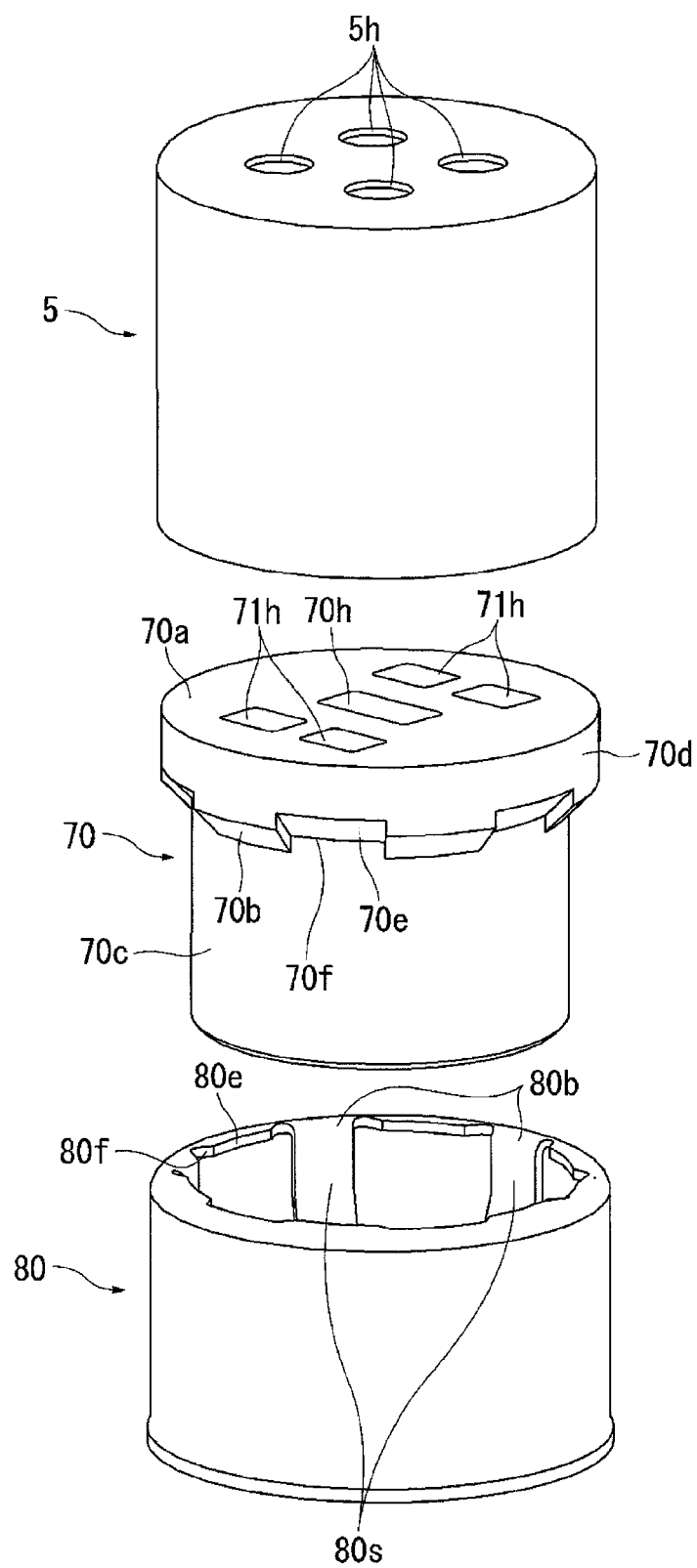
FIG. 2 is an exploded perspective view of a separator and a retainer.
Figure 3:
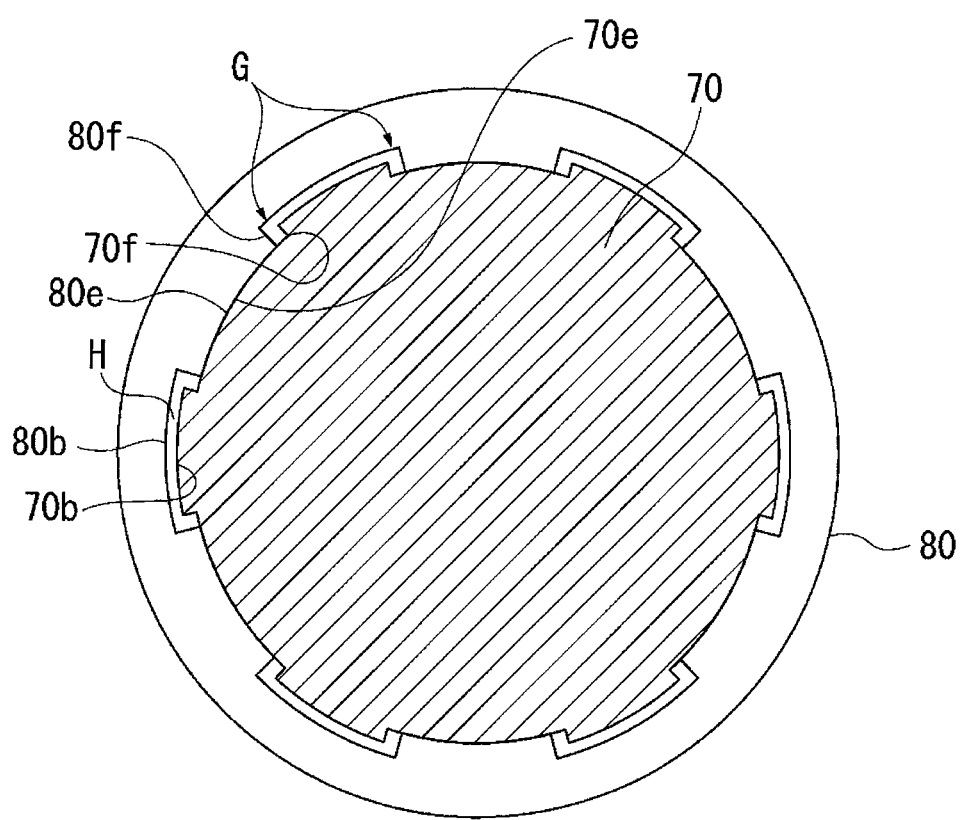
FIG. 3 is a plan view showing the state of engagement between the separator and the retainer.

First, a gas sensor (oxygen sensor) 100 according to a first embodiment of the present invention will be described with reference to FIGS. 1 to 3. FIG. 1 is a cross-sectional view of the gas sensor 100 taken along the direction of an axis O thereof. FIG. 2 is an exploded perspective view of a separator 70 and a retainer 80. FIG. 3 is a plan view showing the state of engagement between the separator 70 and the retainer 80. Notably, the lower side of FIG. 1 (the side where a detection portion 10a of a sensor element 10 is located) will be referred to the "forward side," and the upper side thereof (the side where electrode take-out portions (electrode pads) 10e of the sensor element 10 are located) will be referred to the "rear side."

The gas sensor 100 is an assembly which includes the sensor element 10. The gas sensor 100 includes the plate-shaped sensor element 10 extending in the direction of the axis O (the vertical direction in FIG. 1), and a metallic shell 2 which is to be fixed to an exhaust pipe of an automotive engine. The metallic shell 2 has an approximately cylindrical tubular shape, and has a thread 24 which is formed on the outer surface and is used to fix the gas sensor 100 to the exhaust pipe. The metallic shell 2 has a bore 25 and a ledge portion 2p which projects radially inward from the wall of the bore 25 at the forward end thereof. The metallic shell 2 accommodates the sensor element 10 in the bore 25 and holds the sensor element 10 such that the detection portion 10a provided at the forward end of the sensor element 10 and the electrode pads 10e provided at the rear end of the sensor element 10 protrude from the metallic shell 2. An annular holding member 21 formed of ceramic and surrounding the outer circumferential surface of the sensor element 10, powdery fillers (talc rings) 22, 23, and a sleeve 30 formed of ceramic are disposed between the inner circumferential surface of the metallic shell 2 and the outer circumferential surface of the sensor element 10 such that these members are stacked in this order from the detection portion 10a side. A rear end portion 2a of the metallic shell 2 is crimped so as to press the sleeve 30 toward the forward side. As a result, the holding member 21 is engaged with the ledge portion 2p, and the talc rings 22, 23 are crushed to fill the bore 25, whereby the sensor element 10 is firmly fixed at a predetermined position within the metallic shell 2. Examples of the material to form the talc rings 22, 23 include talc (ceramic powder) and glass (silicate compound such as silicate glass or silicate salt glass).

Notably, the holding member 21 and the talc ring 22 are received in the bore 25 of the metallic shell 2 via a metal cup 20.

Also, an outer protector 4 and an inner protector 3 which are formed of metal and which surround the detection portion 10a of the sensor element 10 are attached to the outer periphery of a forward end portion of the metallic shell 2.

Notably, in this example, the sensor element 10 is an oxygen sensor element configured such that a pair of electrodes are disposed on the surface of a solid electrolyte layer, and a heater for cell activation and an insulating layer (alumina or the like) for protecting the solid electrolyte layer are stacked. Further, a porous protection layer 12 covers the surface of the detection portion 10a of the sensor element 10.

Meanwhile, the electrode pads 10e, which are provided on opposite plate surfaces of a rear end portion of the sensor element 10 (in this example, two electrode pads are provided on each surface, and four electrode pads are provided in total), are surrounded by the cylindrical separator 70 formed of ceramic. As will be described later, the separator 70 has an insertion hole 70h for the sensor element 10 at the center, and holes 71h (see FIG. 2; in this example, the number of the holes is four) which communicate with the insertion hole 70h and which accommodate a plurality of terminal members 60 (in this example, the number of terminal members is 4). The terminal members 60 are inserted into the separated holes 71h so that they are insulated from one another, and the terminal members 60 are electrically connected the corresponding electrode pads 10e of the sensor element 10.

The separator 70 has a main body portion 70c located on the forward side, and a flange portion 70d located on the rear side and projecting from the main body portion 70c such that the flange portion 70d has a larger diameter. The main body portion 70c and the flange 70d are connected by forward-facing surfaces 70b (taper surfaces) whose diameter decreases toward the forward end thereof.

A cylindrical seal member (grommet) 5 formed of rubber is disposed on the rear side of the separator 70 such that the seal member 5 is spaced from the separator 70, and the separator 70 and the grommet 5 are covered by an outer sleeve 90 formed of metal. An annular retainer 80 for holding the separator 70 is fixed, by means of crimping, to the outer sleeve 90 in the vicinity of the center in the direction of the axis O. Further, a portion of the outer sleeve 90 located on the rear side of the crimped portion is reduced in diameter toward the rear side, whereby an inward convex portion 90a is formed. As shown in FIG. 2, the retainer 80 is formed of metal and has an approximately cylindrical shape. The retainer 80 has a plurality of (6 in this example) tabs 80s provided at equal intervals in the circumferential direction. Each tab 80s extends from the rear edge of the retainer 80 toward the inner surface thereof, and has a bent surface 80b.

The bent surfaces 80b of the retainer 80 are mated with the forward-facing surfaces 70b of the separator 70, and the inward convex portion 90a (a forward-facing surface thereof) is engaged with a rearward-facing surface 70a of the separator 70. As a result, the separator 70 is held on the forward and rear sides (lower and upper sides) thereof (is sandwiched between the retainer 80 and the outer sleeve 90 in the direction of the axis O), and the separator 70 is spaced from the metallic shell 2 (the rear end portion 2a thereof) in the direction of the axis O. Also, the tabs 80s butt against the main body portion 70c, and the elastic force of the tabs 80s prevents impacts applied to the outer sleeve 90 from being transmitted directly to the separator 70.

A forward portion of each terminal member 60 held in the separator 70 is bent inward, and its bent portion is electrically connected to the corresponding electrode pad 10e of the sensor element 10. Meanwhile, a rear portion of each terminal member 60 is a crimp portion 65 projecting from the rear end of the separator 70. An end of each lead wire 68 is disposed inside the corresponding crimp portion 65, and is connected thereto through crimping. Each lead wire 68 is passed through a corresponding one of individual through-holes 5h of the grommet 5 (see FIG. 2), and is extended to the outside.

A rear end portion of the outer sleeve 90 is crimped, whereby the grommet 5 is held in the sleeve 90. The outer sleeve 90, which holds the separator 70 and the grommet 5 therein, is fitted onto a rear portion of the metallic shell 2, and welding is performed over the entire circumference of the fitted portion of the outer sleeve 90, whereby the outer sleeve 90 and the metallic shell 2 are connected together.

Next, the structures of the separator 70 and the retainer 80 will be described in detail with reference to FIG. 2.

As shown in FIG. 2, the forward-facing surfaces 70b of the flange portion 70d of the separator 70 serve as contact surfaces which come into contact with the retainer 80 (the bent surfaces 80b thereof). The plurality of (6 in this example) forward-facing surfaces 70b are formed at predetermined intervals in the circumferential direction, and a concave surface 70e is formed between adjacent forward-facing surfaces (contact surfaces) 70b. The concave surface 70e is a taper surface which is located rearward of the forward-facing surfaces 70b. The forward-facing surfaces 70b and the concave surfaces 70e are alternating disposed in the circumferential direction. Therefore, the number of the concave surfaces 70e is also plural (6 in this example).

The concave surfaces 70e decrease in diameter (the diameter of an imaginary circle formed by the concave surfaces) from the flange portion 70d toward the forward end thereof, and reach the main body portion 70c. A rotation restriction surface 70f which forms a step surface parallel to the direction of the axis O is formed between each concave surface 70e and a forward-facing surface 70b located adjacent thereto. Notably, the rotation restriction surface 70f is orthogonal to the circumferential direction of the forward-facing surfaces (contact surfaces) 70b. However, the rotation restriction surface 70f is not required to be orthogonal to the circumferential direction of the forward-facing surfaces (contact surfaces) 70b, so long as each rotation restriction surface 70f has an angle in relation to the circumferential direction of the contact surfaces 70b (is not parallel to the circumferential direction).

Meanwhile, an edge portion 80e is formed between adjacent tabs 80s of the retainer 80. The edge portion 80e extends toward the radially inner side beyond the bent surfaces 80b. The bent surfaces 80b and the edge portions 80e are disposed alternatingly in the circumferential direction. Therefore, the number of the edge portions 80e is also plural (6 in this example). Each side end of each edge portion 80e which faces the corresponding tab 80s forms an engagement surface 80f which has an angle in relation to the circumferential direction of the contact surfaces 70b.

As shown in FIG. 3, when the forward-facing surfaces 70b of the separator 70 are mated with the bent surfaces 80b of the retainer 80, the edge portions 80e enter recesses formed by the concave surfaces 70e, and each engagement surface 80f comes into contact (mates) with a corresponding rotation restriction surface 70f. Since the retainer 80 itself is fixed to the outer sleeve 90, rotation of the separator 70 in the circumferential direction is restricted by the retainer 80. Notably, the hatching in FIG. 3 shows the separator 70.

Notably, in the present invention, rotation of the separator 70 in the circumferential direction is not required to be prevented completely, and the separator 70 may rotate within an angle within which the rotation of the separator 70 does not affect the connection between the terminal members 60 and the electrode pads 10e. In this case, each edge portion 80e does not mate with the corresponding concave surface 70e tightly in the circumferential direction, and the edge portion 80e mates with the corresponding concave surfaces 70e while forming a play G therebetween in the circumferential direction. Therefore, the rotation restriction surfaces 70f come into contact with the corresponding engagement surfaces 80f upon slight rotation of the separator 70 in the circumferential direction. However, such a play may be provided in consideration of machining accuracy, etc.

Also, in the present embodiment, each bent surface 80b of the retainer 80 and a corresponding forward-facing surface 70b of the separator 70 do not come into contact with each other, and a gap H is formed therebetween. It is sufficient that the concave surfaces 70e are in contact with the edge portions 80e.

As described above, in the present embodiment, it is possible to separate the grommet 5 from the separator 70 to thereby suppress thermal deterioration of the grommet 5. Also, instead of pressing the grommet 5, the inward convex portion 90a of the outer sleeve 90 is caused to press the rearward-facing surface 70a of the separator 70 toward the forward side. Therefore, the separator 70 can be held between the retainer 80 and the inward convex portion 90a easily and reliably. Moreover, rotation of the separator 70, which would otherwise occur due to separation of the grommet 5 from the separator 70, can be readily restricted by providing the engagement surfaces 80f and the rotation restriction surfaces 70f on the retainer 80 and the separator 70, respectively, without providing a separate member for rotation restriction.

Figure 4:
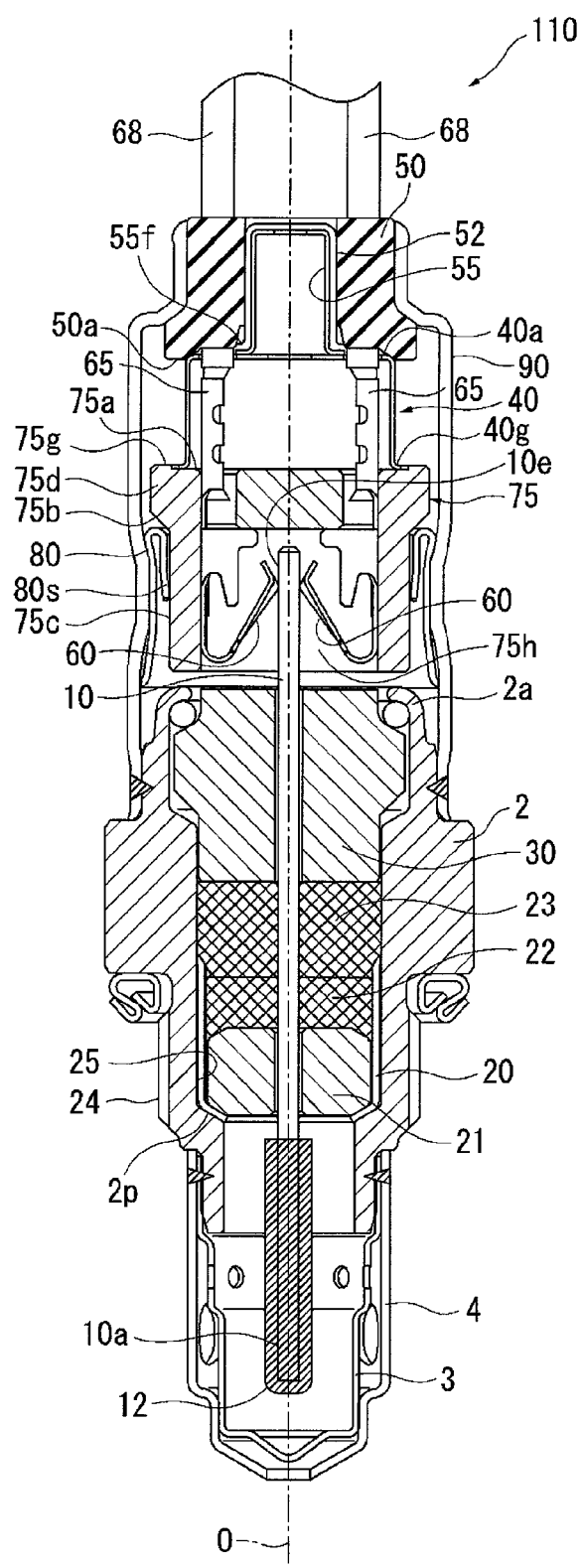
FIG. 4 is a cross-sectional view of a gas sensor according to a second embodiment of the present invention taken along the axial direction thereof.
Figure 5:
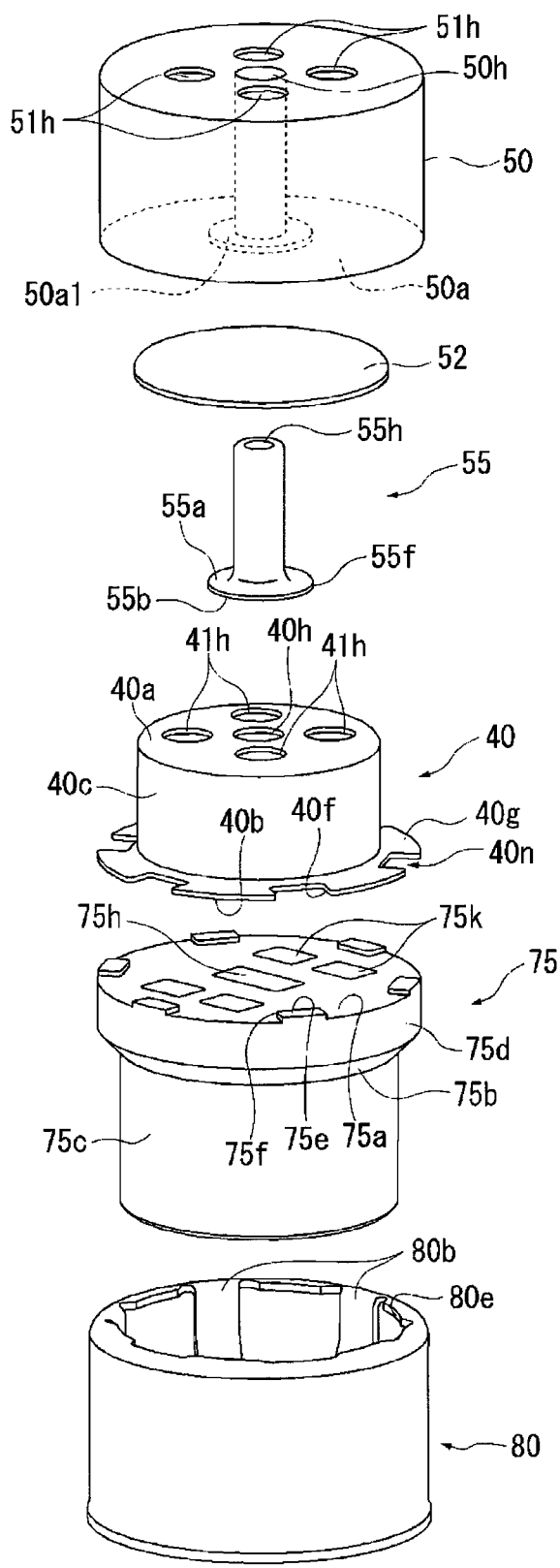
FIG. 5 is an exploded perspective view of a separator, a retainer, and an inner sleeve.
Figure 6:
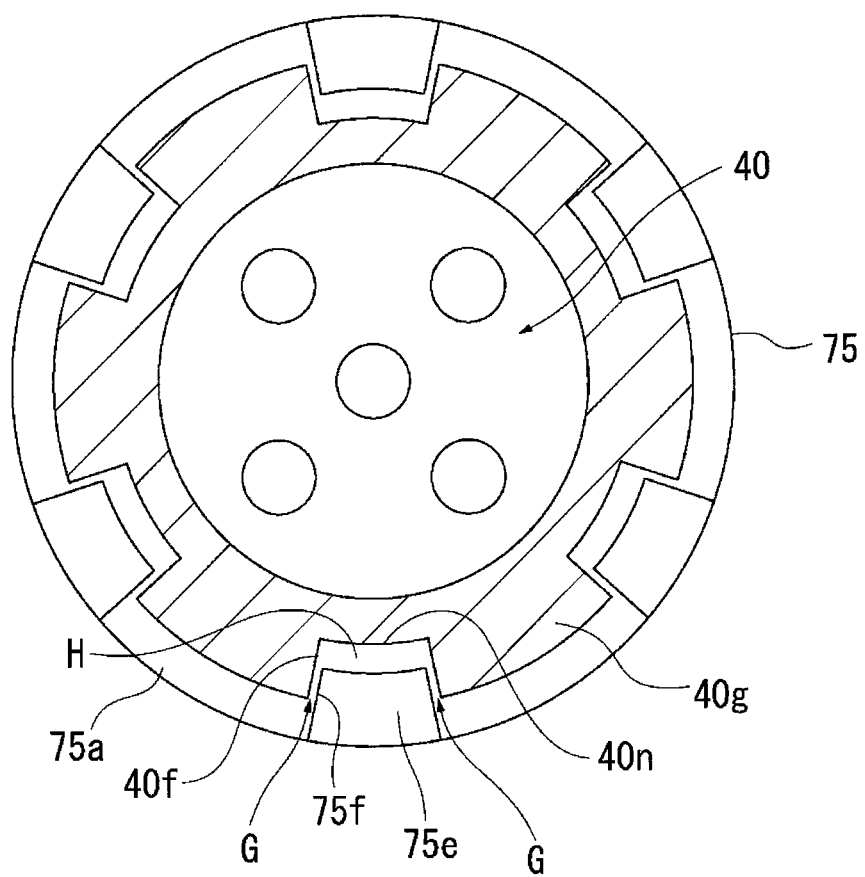
FIG. 6 is a plan view showing the state of engagement between the separator and the inner sleeve.

Next, a gas sensor (oxygen sensor) 110 according to a second embodiment of the present invention will be described with reference to FIGS. 4 to 6. FIG. 4 is a cross-sectional view of the gas sensor 110 taken along the direction of the axial O thereof. FIG. 5 is an exploded perspective view of a separator 75, a retainer 80, and an inner sleeve 40. FIG. 6 is a plan view showing the state of engagement between the separator 75 and the inner sleeve 40.

Notably, portions of the gas sensor 110 of the second embodiment which are identical in structure with those of the gas sensor 100 of the first embodiment are denoted by the same reference numerals, and their descriptions are omitted. The gas sensor 110 differs from the gas sensor 100 of the first embodiment in that the gas sensor 110 has the inner sleeve 40, the outer sleeve 90 does not have the inward convex portion 90a, and the separator 75 and the seal member (grommet) 50 have structures different from those of the separator and the seal member of the gas sensor 100.

As shown in FIG. 4, the inner sleeve 40 formed of metal and having the form of a bottomed cylindrical tube having a closed rear end is disposed inside the outer sleeve 90 to be located between the grommet 50 and the separator 75. The inner sleeve 40 has a tubular portion extending in the axial direction, and an extension portion 40a extending radially inward from the rear end of the tubular portion. A flange portion 40g projects radially outward from the forward end of the inner sleeve 40 (see FIG. 5). A forward-facing surface 40b (FIG. 5) of the flange portion 40g is in contact with a rearward-facing surface 75a of the separator 75, and the extension portion 40a is in contact with a forward-facing surface 50a of the grommet 50. A rear end portion of the outer sleeve 90 is crimped, whereby the grommet 50 is held within the outer sleeve 90, and the grommet 50 presses the inner sleeve 40 toward the separator 75, whereby the inner sleeve 40 is held within the outer sleeve 90.

The edge portions 80e of the retainer 80 engage with a forward-facing surface (contact surface) 75b of the separator 75, and the forward-facing surface 40b of the inner sleeve 40 engages with the rearward-facing surface 75a of the separator 75. As a result, the separator 75 is held on the forward and rear sides (lower and upper sides) thereof (is sandwiched between the retainer 80 and the inner sleeve 40 in the direction of the axis O), and the separator 75 is spaced from the metallic shell 2 (the rear end portion 2a thereof).

As shown in FIG. 5, like the separator 70, the separator 75 has a main body portion 75c provided on the forward side, and a flange portion 75d provided on the rear side such that the flange portion 75d projects from the main body portion 75c and has a larger diameter. The main body portion 75c and the flange portion 75d are connected together by a forward-facing surface 75b (taper surface) whose diameter decreases toward the forward end. The separator 75 has an insertion hole 75h for the sensor element 10 at the center, and holes 75k (in this example, the number of the holes is four) which communicate with the insertion hole 75h and which accommodate the plurality of terminal members 60 (in this example, the number of terminal members is 4).

As described above, in the second embodiment, the inner sleeve 40 is disposed between the grommet 50 and the separator 75; however, the contact area between the inner sleeve 40 and the separator 75 is small. Therefore, transmission of heat from the separator 70 to the grommet 50 decreases, whereby thermal deterioration of the grommet 50 can be suppressed. Also, since the separator 75 is pressed forward by the grommet 50 via the inner sleeve 40, the separator 75 can be held between the retainer 80 and the inner sleeve 40 easily and reliably. Notably, although the edge portions 80e come into contact with the forward-facing surface (contact surface) 75b, the bent surfaces 80b are disposed such that a clearance is formed between each bent surface 80b and the forward-facing surface 75b. This is because, if the bent surfaces 80b are in contact with the forward-facing surface 75b, the bent surfaces 80b are influenced by, for example, vibration of the separator 75 during use of the gas sensor.

Meanwhile, in the second embodiment, the rotation restriction surfaces and the engagement surfaces are not formed on the retainer 80. Also, the contact surface between the forward-facing surface 40b of the inner sleeve 40 and the separator 75 is small, and the frictional resistance therebetween is small. Therefore, rotation of the separator 75 in the circumferential direction cannot be restricted by the pressing force of the inner sleeve 40 only.

In view of this, in the second embodiment, as shown in FIG. 5, rotation restriction surfaces 75f and engagement surfaces 40 are provided on the separator 75 and the inner sleeve 40, respectively. Notably, since the inner sleeve 40 is in contact with the forward-facing surface 50a of the grommet 50 in a large area, the inner sleeve 40 itself hardly rotates in the circumferential direction because of the frictional force between the inner sleeve 40 and the grommet 50. Therefore, rotation of the separator 75 in the circumferential direction is restricted by the inner sleeve 40.

Specifically, as shown in FIG. 5, a plurality of (6 in this example) rectangular projections 75e are formed along the peripheral edge of the rearward-facing surface 75a of the separator 75 at equal intervals in the circumferential direction. Each side wall 75f of each rectangular projection 75e is orthogonal to the circumferential direction of the forward-facing surface (contact surface) 75b and serves as a rotation restriction surface which has "an angle in relation to the circumferential direction of the contact surface 75b." However, the rotation restriction surfaces 75f are not required to be orthogonal to the circumferential direction of the contact surface 75b, so long as each rotation restriction surface 75f has an angle in relation to the circumferential direction of the forward-facing surface (contact surface) 75b (is not parallel to the circumferential direction).

Meanwhile, the flange portion 40g of the inner sleeve 40 has a plurality of (6 in this example) cutouts 40n at equal intervals in the circumferential direction. The cutouts 40n extend radially inward from the peripheral edge of the flange portion 40g. Thus, the flange portion 40g has the shape of flower petals as viewed from above. Each side end of each cutout 40n forms an engagement surface 40f which has an angle in relation to the circumferential direction of the contact surface 75b.

As shown in FIG. 6, when the inner sleeve 40 is placed on the rearward-facing surface 75a of the separator 70, the rectangular projections 75e enter the cutouts 40n, and the rotation restriction surfaces 75f come into contact (mate) with the corresponding engagement surfaces 40f. Since the inner sleeve 40 itself hardly rotates in the circumferential direction, rotation of the separator 75 in the circumferential direction is restricted by the inner sleeve 40. Notably, the hatched portion in FIG. 6 shows the flange portion 40g.

In the second embodiment as well, the separator 75 may rotate slightly in the circumferential direction. In this case, each rectangular projection 75e does not mate with the corresponding cutout 40n tightly in the circumferential direction, and each rectangular projection 75e mates with the corresponding cutout 40n while forming a play G therebetween in the circumferential direction. Also, a clearance H in the radial direction may be formed between each rectangular projection 75e and the bottom of the corresponding cutout 40n.

As described above, in the second embodiment, the inner sleeve 40 is interposed between the grommet 50 and the separator 75, whereby transfer of heat from the separator 75 to the grommet 50 decreases. Therefore, thermal deterioration of the grommet 50 can be suppressed. Also, since the separator 75 is pressed forward by the grommet 50 via the inner sleeve 40, the separator 75 can be held between the retainer 80 and the inner sleeve 40 easily and reliably. Moreover, rotation of the separator 75, which would otherwise occur due to separation of the grommet 50 from the separator 75, can be readily restricted by providing the engagement surfaces 40f and the rotation restriction surfaces 75f on the inner tube 40 and the separator 75, respectively, without providing a separate member for rotation restriction.

Notably, as shown in FIG. 5, in the second embodiment, a gas passage hole 50h is formed at the center of the grommet 50 such that the gas passage hole 50h extends therethrough in the direction of the axis O, and a tubular filter retainer 55 and a water-repellent gas passage filter 52 covering the outer side of the filter retainer 55 are inserted into the gas passage hole 50h. This structure allows introduction of a reference gas (atmosphere) from the outside of the grommet 50 into the gas sensor. The gas passage filter 52, which is formed of fluorocarbon resin such as PTFE (polytetrafluoroethylene), allows air to pass therethrough but does not allow water droplets to pass therethrough.

The filter retainer 55 is formed of metal, and has the form of a bottomed cylindrical tube having a closed rear end. A center hole 55h is formed in the rearward-facing surface of the filter retainer 55, and the reference atmosphere enters from the center hole 55h and flows into the gas sensor through the gas passage filter 52. Meanwhile, a collar portion 55f projects radially outward from the forward end of the filter retainer 55. Also, on the side toward the forward-facing surface 50*a* of the grommet 50, a recess 50*a*1 extending rearward is formed around the circumferential edge of the gas passage hole 50*h*. The rearward-facing surface 55*a* of the collar portion 55*f* comes into contact with the bottom of the recess 50*a*1 (is received by the recess 50*a*1) whereby rearward coming off of the filter retainer 55 is prevented.

Meanwhile, forward coming off of the filter retainer 55 is prevented by the frictional force between the wall surface of the recess 50*a*1 and the collar portion 55*f*. However, the filter retainer 55 may come off toward the forward side due to vibration or the like during use of the gas sensor. Such forward coming off of the filter retainer 55 can be prevented by bringing the extension portion 40*a* of the inner sleeve 40 into contact with the forward-facing surface 55*b* of the collar portion 55*f*.

Notably, a through-hole 40*h* which communicates with the interior of the filter retainer 55 is formed in the extension portion 40*a* of the inner sleeve 40. In order to prevent the filter retainer 55 from passing through the through-hole 40*h* and coming off, it is necessary to prevent the through-hole 40*h* from completely overlapping with the collar portion 55*f*. In the present embodiment, since the diameter of the collar portion 55*f* is made larger than the diameter of the through-hole 40*h*, it is possible to prevent the filter retainer 55 from passing through the through-hole 40*h* and coming off.

Also, the lead wires 68 are passed through lead holes 41*h* which penetrate the extension portion 40*a* of the inner sleeve 40 and through lead holes 51*h* of the grommet 50, and are extended to the outside.

Figure 7:
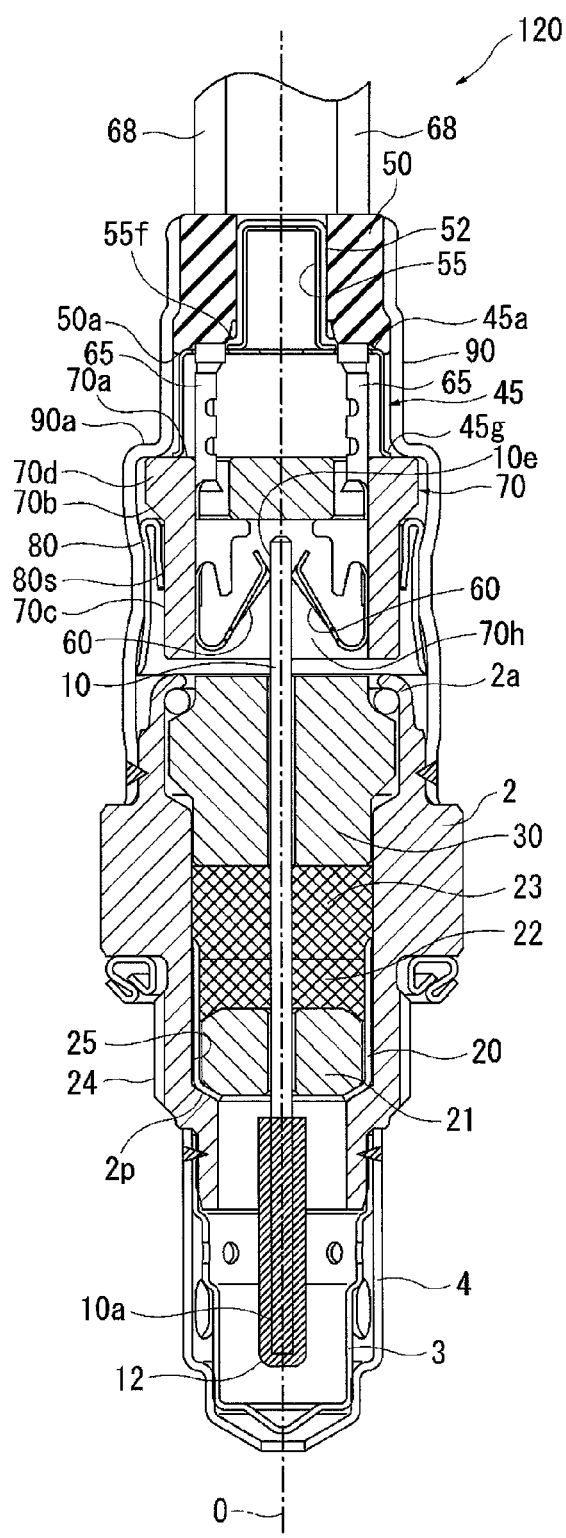
FIG. 7 is a cross-sectional view of a gas sensor according to a third embodiment of the present invention taken along the axial direction thereof.
Figure 8:
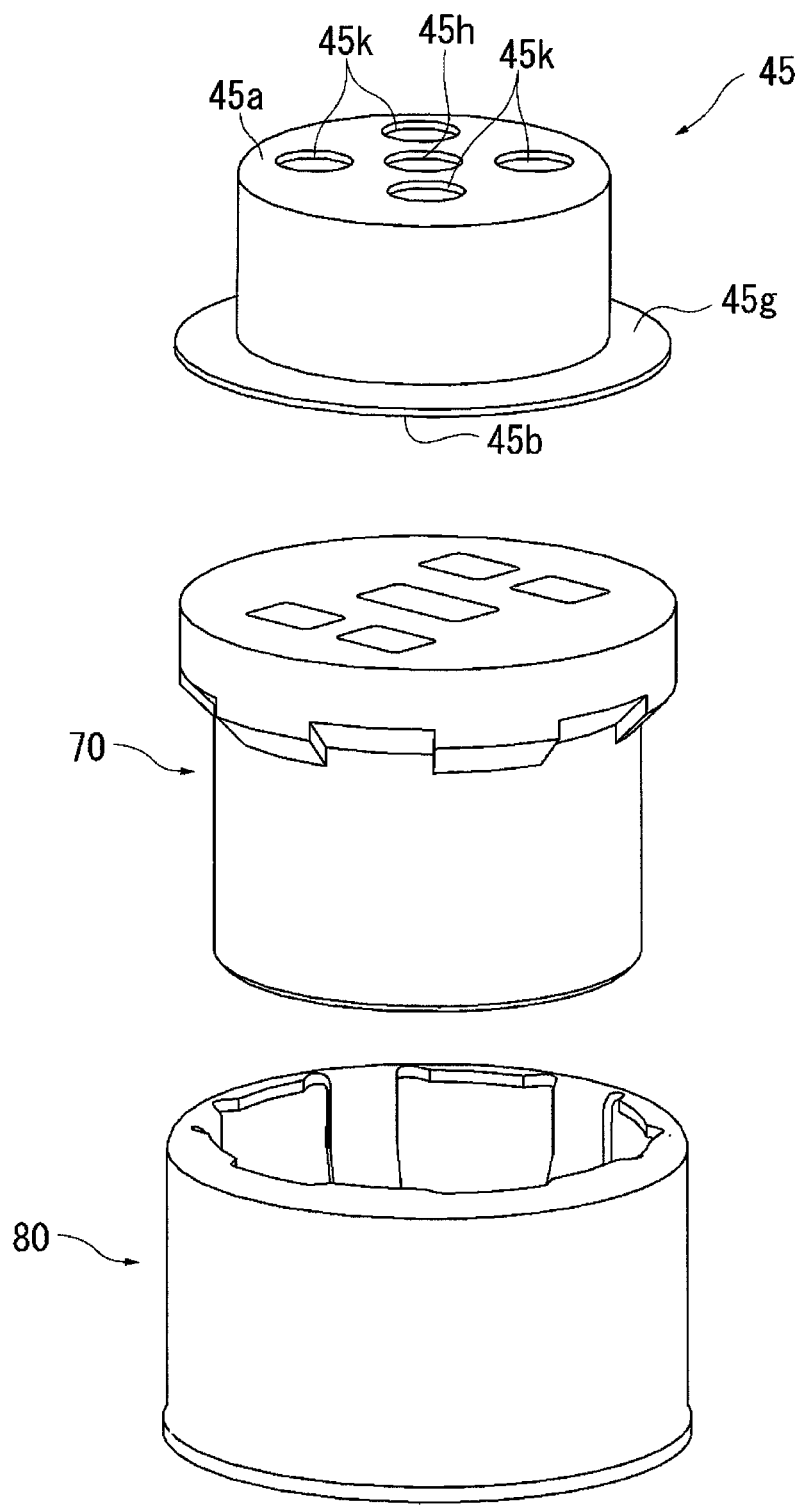
FIG. 8 is an exploded perspective view of a separator, a retainer, and an inner sleeve.

Next, a gas sensor (oxygen sensor) 120 according to a third embodiment of the present invention will be described with reference to FIGS. 7 and 8. FIG. 7 is a cross-sectional view of the gas sensor 120 taken along the direction of the axial O thereof. FIG. 8 is an exploded perspective view of a separator 70, a retainer 80, and an inner sleeve 45.

Notably, portions of the gas sensor 120 of the third embodiment which are identical in structure with those of the gas sensor 100 of the first embodiment and the gas sensor 110 of the second embodiment are denoted by the same reference numerals, and their descriptions are omitted.

The gas sensor 120 has a structure obtained by combining the structures of the gas sensors 100 and 110.

Namely, the gas sensor 120 has the same separator 70 and the same retainer 80 as the gas sensor 100, and, as in the case of the first embodiment, rotation of the separator 70 can be readily restricted by the engagement surfaces 80*f* and the rotation restriction surfaces 70*f* provided on the retainer 80 and the separator 70, respectively.

The gas sensor 120 also has an inner sleeve 45 similar to the inner sleeve 40 of the gas sensor 110. The inner sleeve 45 has an extension portion 45*a* extending radially inward from the rear end of the tubular portion thereof, and a flange portion 45*g* projecting radially outward from the forward end of the inner sleeve 45. Therefore, as in the case of the second embodiment, the inner sleeve 45 is interposed between the grommet 50 and the separator 70, and transfer of heat from the separator 70 to the grommet 50 decreases. Therefore, thermal deterioration of the grommet 50 can be suppressed. Also, since the separator 70 is pressed forward by the grommet 50 via the inner sleeve 45, the separator 70 can be held between the retainer 80 and the inner sleeve 45 easily and reliably.

Moreover, as in the case of the first embodiment, the inward convex portion 90*a* is provided on the outer sleeve 90. Therefore, the separator 70 can be pressed forward by the inward convex portion 90*a* as well, whereby the separator 70 can be held more stably.

However, since no cutout is formed in the flange portion 45*g* and the inner sleeve 45 has no engagement surface, the inner sleeve 45 does not have the function of restricting rotation of the separator 70.

Notably, like the inner sleeve 40, a through-hole 45*h* which communicates with the interior of the filter retainer 55 and lead holes 45*k* through which the lead wires 68 are passed are formed in the extension portion 45*a* of the inner sleeve 45. In the case of the third embodiment as well, forward coming off of the filter retainer 55 can be prevented by bringing the extension portion 45*a* of the inner sleeve 45 into contact with the forward-facing surface 55*b* (see FIG. 5) of the collar portion 55*f*.

Figure 9:
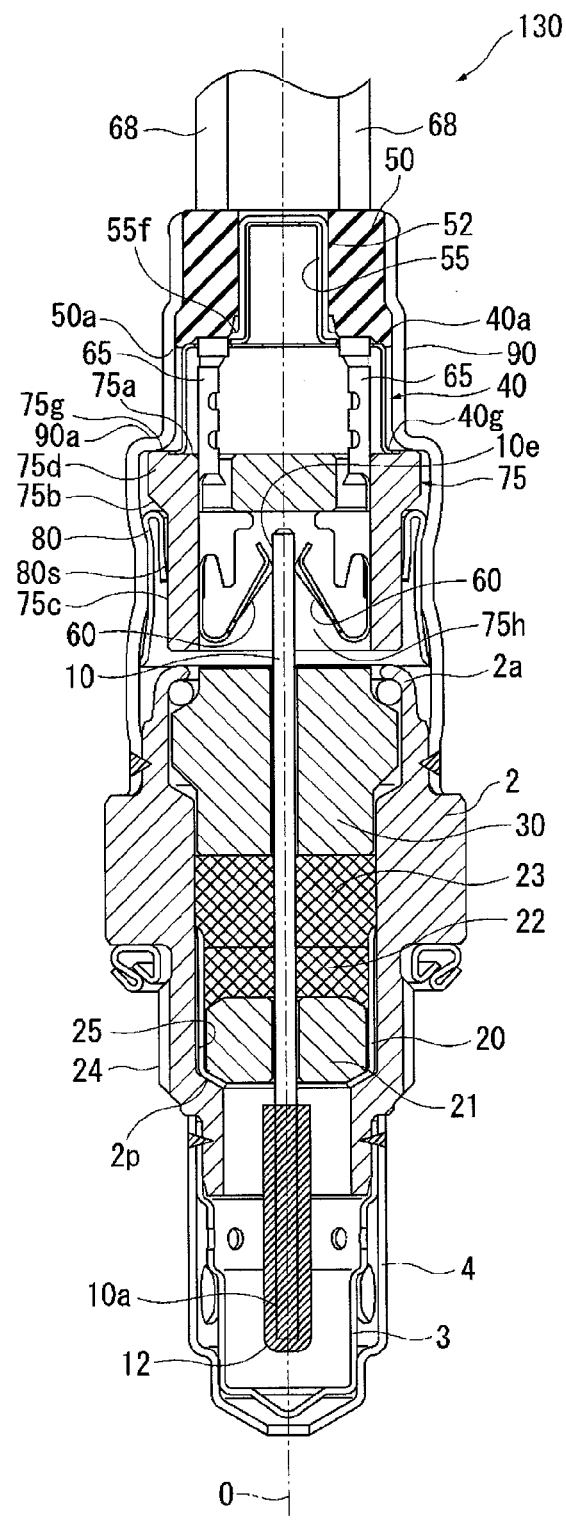
FIG. 9 is a cross-sectional view of a gas sensor according to a fourth embodiment of the present invention taken along the axial direction thereof.

Next, a gas sensor (oxygen sensor) 130 according to a fourth embodiment of the present invention will be described with reference to FIG. 9. FIG. 9 is a cross-sectional view of the gas sensor 130 taken along the direction of the axial O thereof.

Notably, portions of the gas sensor 130 of the fourth embodiment which are identical in structure with those of the gas sensors 100 and 110 are denoted by the same reference numerals, and their descriptions are omitted.

The gas sensor 130 has a structure obtained by combining the structures of the gas sensors 100 and 110.

Namely, the gas sensor 130 has the same separator 75 and the same inner sleeve 40 as the gas sensor 110, and, as in the case of the second embodiment, rotation of the separator 75 can be readily restricted by the engagement surfaces 40*f* and the rotation restriction surfaces 75*f* provided on the inner sleeve 40 and the separator 75, respectively.

Also, as in the case of the second embodiment, the inner sleeve 40 is interposed between the grommet 50 and the separator 75, whereby transfer of heat from the separator 75 to the grommet 50 decreases. Therefore, thermal deterioration of the grommet 50 can be suppressed. Also, since the separator 75 is pressed forward by the grommet 50 via the inner sleeve 40, the separator 75 can be held between the retainer 80 and the inner sleeve 40 easily and reliably.

Moreover, as in the case of the first embodiment, the inward convex portion 90*a* is provided on the outer sleeve 90. Therefore, the separator 75 can be pressed forward by the inward convex portion 90*a* as well, whereby the separator 75 can be held more stably.

Needles to say, the present invention is not limited to the above-described embodiments, and encompasses various modifications and equivalents which fall within the scope of the present invention. For example, the shapes of the separator and the inner sleeve are not limited to the above-described shapes.

The present invention can be applied not only to oxygen sensors, but also to NOx sensors and other gas sensors for measuring the concentration of gas such as HC or $H_2$.

The position of the extension portion 40*a* of the inner sleeve 40 is not limited to the rear end of the tubular portion.

The shape of the gas passage filter 52 is not limited to a sheet-like shape, and may be a circular columnar shape or a cylindrical tubular shape. The collar portion 55*f* may be omitted in the case where the diameter of the filter retainer 55 is larger than the diameter of the through-hole 40*h*. In this case, the forward edge of the filter retainer 55 comes into contact with the extension portion 40*a* of the inner sleeve 40.

Figure 10:
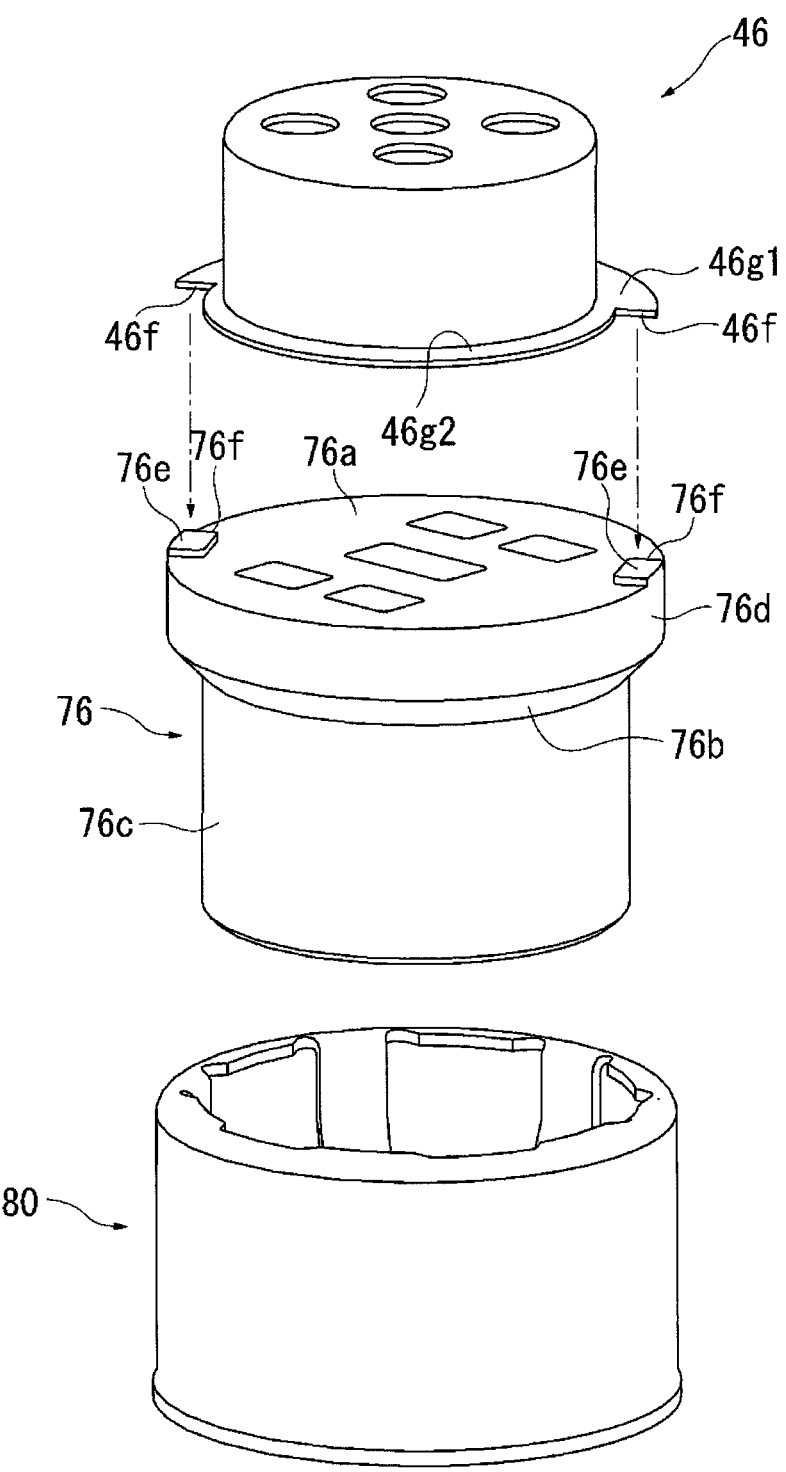
FIG. 10 is an exploded perspective view of a separator and an inner sleeve according to a modification of the second embodiment.

For example, the second embodiment may be modified to use a separator 76 and an inner sleeve 46 as shown in FIG. 10. As shown in FIG. 10, like the separator 75, the separator 76 has a main body portion 76*c* provided on the forward side, and a flange portion 76d provided on the rear side such that the flange portion 76d projects from the main body portion 76c and has a larger diameter. The main body portion 76c and the flange portion 76d are connected together by a forward-facing surface 76b (taper surface) whose diameter decreases toward the forward end. The forward-facing surface 76b comes into engagement with the edge portions 80e (not shown) of the retainer 80. The separator 76 has a pair of rectangular projections 76e formed along the peripheral edge of the rearward-facing surface 76a thereof at diametrically opposite positions. Each of side walls 76f of the rectangular projections 76e, which walls face the same side (the back side of the sheet of FIG. 10), is orthogonal to the circumferential direction of the forward-facing surface (contact surface) 76b and serves as a rotation restriction surface which "has an angle in relation to the circumferential direction of the contact surface 76b."

Meanwhile, the inner sleeve 46 has the shape of a bottomed cylindrical tube like the inner sleeve 40, and has first and second flange portions 46g1 and 46g2 projecting radially outward from the forward end of the inner sleeve 46. Each of the first and second flange portions 46g1 and 46g2 has an arcuate shape, and the first flange portion 46g1 is larger in diameter than the second flange portion 46g2. Each of the side ends of the first flange portion 46g1 located at the boundaries between the first flange portion 46g1 and the second flange portion 46g2 forms an engagement surface 46f which is orthogonal to the circumferential direction of the contact surface 76b.

Accordingly, when the inner sleeve 46 is disposed on the rearward-facing surface 76a of the separator 76, the first flange portion 46g1 is located on the back side of the pair of rectangular projections 76e with respect to the front-to-back direction of the sheet, and the rotation restriction surfaces 76f come into contact with the engagement surfaces 46f. Therefore, rotation of the separator 76 in the circumferential direction is restricted.

Figure 11:
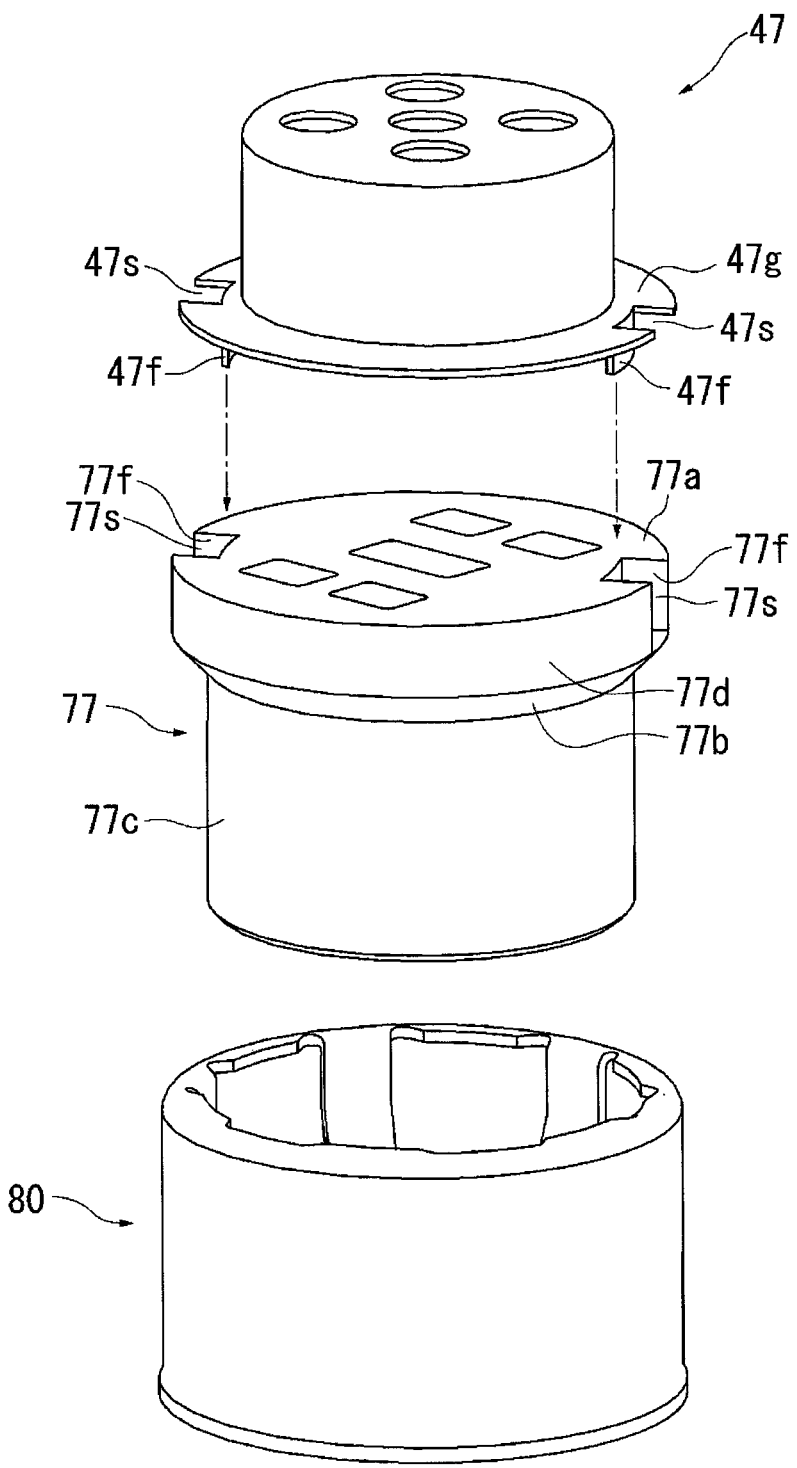
FIG. 11 is an exploded perspective view of a separator and an inner sleeve according to another modification of the second embodiment.

Also, the second embodiment may be modified to use a separator 77 and an inner sleeve 47 as shown in FIG. 11. As shown in FIG. 11, like the separator 75, the separator 77 has a main body portion 77c provided on the forward side, and a flange portion 77d provided on the rear side such that the flange portion 77d projects from the main body portion 77c and has a larger diameter. The main body portion 77c and the flange portion 77d are connected together by a forward-facing surface 77b (taper surface) whose diameter decreases toward the forward end. The forward-facing surface 77b comes into engagement with the edge portions 80e (not shown) of the retainer 80. The separator 77 has two grooves 77s formed along the peripheral edge of the rearward-facing surface 77a thereof at diametrically opposite positions such that the grooves 77s extend forward from the peripheral edge of the rearward-facing surface 77a along the side wall of the separator 77 to positions slightly shifted rearward from the forward-facing surface 77b. Each of side walls of each groove 77s is orthogonal to the circumferential direction of the forward-facing surface (contact surface) 77b and serves as a rotation restriction surface which has "an angle in relation to the circumferential direction of the contact surface 77b."

Meanwhile, the inner sleeve 47 has the shape of a bottomed cylindrical tube like the inner sleeve 40, and has a flange portions 47g projecting radially outward from the forward end of the inner sleeve 47. The flange portion 47g has a pair of rectangular cutouts at diametrically opposite positions. Each of the cutouts is formed by bending a rectangular tab 47s toward the forward side. Each of opposite side ends of the tab 47s forms an engagement surface 47f which is orthogonal to the circumferential direction of the contact surface 77b.

Accordingly, when the inner sleeve 47 is disposed on the rearward-facing surface 77a of the separator 77, the rectangular tabs 47s are inserted into the pair of grooves 77s, and each rotation restriction surface 77f comes into contact with the corresponding engagement surface 47f. Therefore, rotation of the separator 77 in the circumferential direction is restricted.

Figure 12:
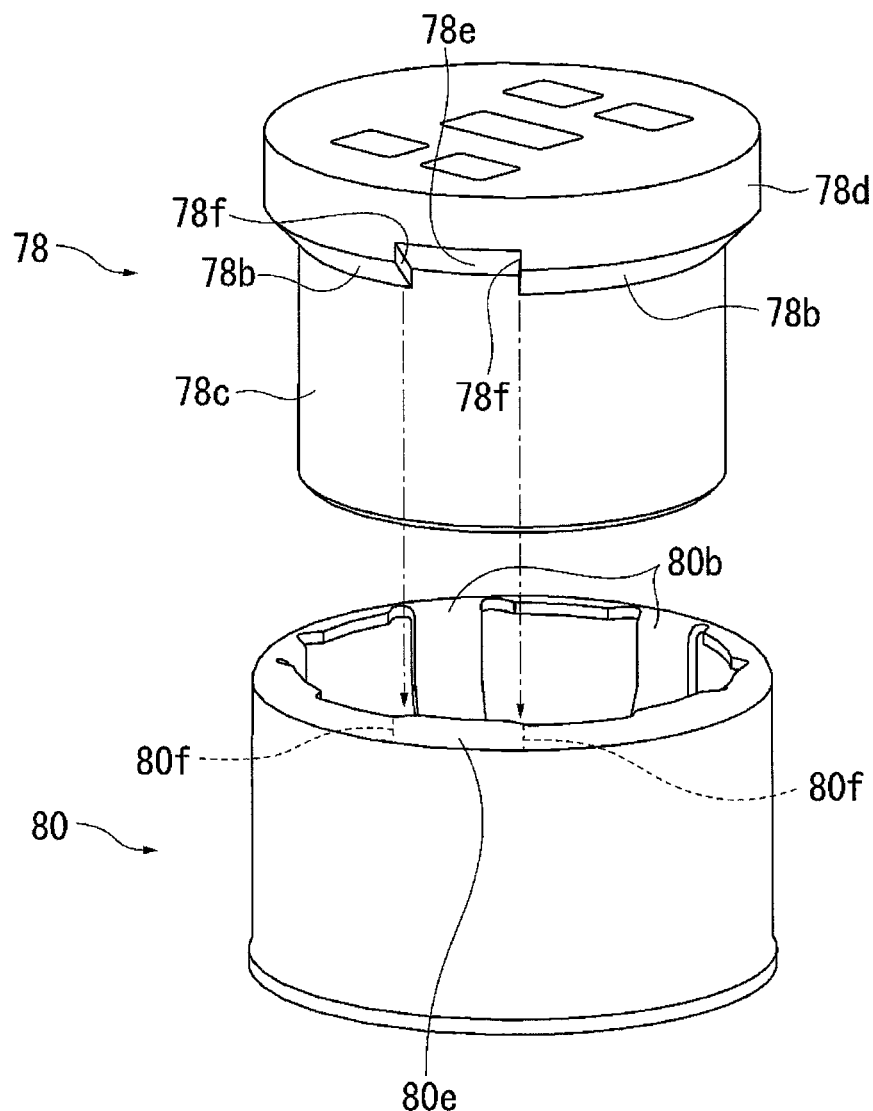
FIG. 12 is an exploded perspective view of a separator according to a modification of the first embodiment.

The first embodiment may be modified to use a separator 78 as shown in FIG. 12.

As shown in FIG. 12, like the separator 70, the separator 78 has a main body portion 78c provided on the forward side, and a flange portion 78d provided on the rear side such that the flange portion 78d projects from the main body portion 78c and has a larger diameter. The main body portion 78c and the flange portion 78d are connected together by a forward-facing surface 78b (taper surface) whose diameter decreases toward the forward end. The forward-facing surface 78b serves as a contact surface which comes into engagement with the edge portions 80e (not shown) of the retainer 80. Also, the separator 78 has a single concave surface 78e which is a taper surface which is formed by depressing the forward-facing surface (contact surface) 78b rearward with respect to the direction of the axis O.

The concave surface 78e decreases in diameter from the flange portion 78d toward the forward end thereof, and reaches the main body portion 78c. A pair of rotation restriction surfaces 78f which are parallel to the direction of the axis O are formed between the concave surface 78e and the forward-facing surface 78b. Each rotation restriction surface 78f is orthogonal to the circumferential direction of the forward-facing surface (contact surface) 78b, and "has an angle in relation to the circumferential direction of the contact surface 78b."

When the separator 78 is fitted into the retainer 80, the edge portion 80e enters the concave surface 78e for engagement therewith, and the engagement surfaces 80f come into contact with the rotation restriction surfaces 78f. Since the retainer 80 itself is fixed to the outer sleeve 90, rotation of the separator 78 in the circumferential direction is restricted.

Figure 13:
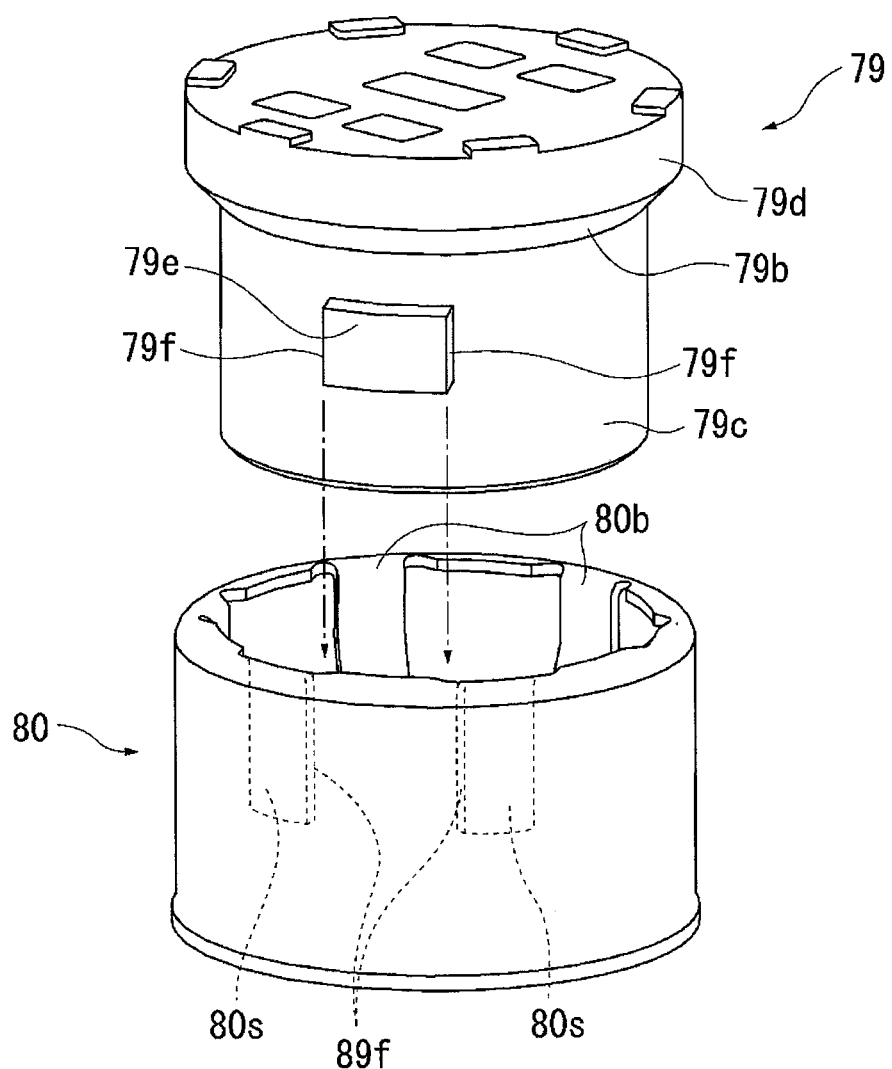
FIG. 13 is an exploded perspective view of a separator according to another modification of the first embodiment.

The first embodiment may be modified to use a separator 79 as shown in FIG. 13.

As shown in FIG. 13, like the separator 70, the separator 79 has a main body portion 79c provided on the forward side, and a flange portion 79d provided on the rear side such that the flange portion 79d projects from the main body portion 79c and has a larger diameter. The main body portion 79c and the flange portion 79d are connected together by a forward-facing surface 79b (taper surface) whose diameter decreases toward the forward end. The forward-facing surface 79b serves as a contact surface which comes into engagement with the edge portions 80e (not shown) of the retainer 80. Also, the separator 79 has a single rectangular projection 79e formed on the main body portion 79c at a position located forward of the forward-facing surface (contact surface) 79b. Each of opposite side surfaces of the rectangular projection 79e serves as a rotation restriction surface 79f which is orthogonal to the circumferential direction of the forward-facing surface (contact surface) 79b, and "has an angle in relation to the circumferential direction of the contact surface 79b."

When the separator 79 is fitted into the retainer 80, the rectangular projection 79e enters the space between adjacent tabs 80s, the rotation restriction surfaces 79f come into contact with the side ends (engagement surfaces) 89f of the tabs 80*s*. Since the retainer 80 itself is fixed to the outer sleeve 90, rotation of the separator 79 in the circumferential direction is restricted.

DESCRIPTION OF REFERENCE NUMERALS

2: metallic shell
10: sensor element
10*a*: detection portion
40, 45, 46, 47: inner sleeve
40*a*, 45*a*: extension portion of the inner sleeve
40*b*, 45*b*: forward-facing surface of the inner sleeve
5, 50: seal member (grommet)
50*a*: forward-facing surface of the seal member (grommet)
50*h*: gas passage hole of the seal member (grommet)
52: gas passage filter
55: filter retainer
55*a*: rearward-facing surface of the collar portion
55*b*: forward-facing surface of the collar portion
55*f*: collar portion of the filter retainer
70-79: separator
70*a*-79*a*: rearward-facing surface of the separator
70*b*-79*b*: contact surface of the separator
70*d*-79*d*: flange portion of the separator
70*f*-79*f*: rotation restriction surface
80: retainer
40*f*, 46*f*, 47*f*, 80*f*, 89*f*: engagement surface
90: outer sleeve
90*a*: inward convex portion of the outer sleeve
100-130: gas sensor
O: axial direction

The invention claimed is:

1. A gas sensor comprising:
a sensor element extending in an axial direction and having a detection portion at a forward end thereof;
a tubular metallic shell surrounding an outer circumferential surface of the sensor element;
a tubular separator having a flange portion and surrounding the sensor element, the separator being spaced from the metallic shell;
a tubular outer sleeve covering the separator and disposed on a rear side of the metallic shell, the outer sleeve having an inward convex portion which abuts a rearward-facing surface of the separator and restricts reward movement of the separator;
a seal member disposed on a rear side of the separator and accommodated in a rear end portion of the outer sleeve such that the seal member is spaced from the separator; and
an annular retainer fixed to the outer sleeve and being in contact with a contact surface that forms at least a portion of a forward-facing surface of the flange portion, wherein
the separator has a rotation restriction surface which restricts rotation of the separator in a circumferential direction, and
the retainer has an engagement surface which comes into contact with the rotation restriction surface.

2. The gas sensor according to claim 1, wherein
a plurality of the contact surfaces are formed on the forward-facing surface of the flange portion at predetermined intervals in the circumferential direction; and
the rotation restriction surface is formed between adjacent ones of the contact surfaces.

3. The gas sensor according to claim 1, further comprising:
an inner sleeve which is disposed inside the outer sleeve and which has a tubular portion extending in the axial direction and an extension portion extending radially inward from the tubular portion, a forward-facing surface of the inner sleeve being in contact with the rearward-facing surface of the separator, wherein a forward-facing surface of the seal member is in contact with the extension portion of the inner sleeve.

4. A gas sensor comprising:
a sensor element having a detection portion at a forward end thereof;
a tubular metallic shell surrounding an outer circumferential surface of the sensor element;
a tubular separator having a flange portion and surrounding the sensor element, the separator being spaced from the metallic shell;
a tubular outer sleeve covering the separator and disposed on a rear side of the metallic shell;
an inner sleeve disposed inside the outer sleeve and having a tubular portion extending in the axial direction and an extension portion extending radially inward from the tubular portion, a forward-facing surface of the inner sleeve abutting the rearward-facing surface of the separator;
a seal member having a forward-facing surface in contact with the extension portion of the inner sleeve and accommodated in a rear end portion of the outer sleeve such that the seal member is spaced from the separator; and
an annular retainer fixed to the outer sleeve and being in contact with a contact surface forming at least a portion of a forward-facing surface of the flange portion, wherein
the separator has a rotation restriction surface which restricts rotation of the separator in a circumferential direction, and
the inner sleeve has an engagement surface which comes into contact with the rotation restriction surface.

5. The gas sensor according to claim 4, wherein
a plurality of the contact surfaces are formed on the rearward-facing surface of the separator at predetermined intervals in the circumferential direction; and
the rotation restriction surface is formed between adjacent ones of the contact surfaces.

6. The gas sensor according to claim 3, wherein
the seal member has a gas passage hole extending therethrough in the axial direction, and
a water-repellent gas passage filter is inserted into the gas passage hole, the gas passage filter having a forward-facing surface in contact with the extension portion of the inner sleeve.

7. The gas sensor according to claim 6, wherein
a through-hole which communicates with the gas passage hole is formed in the extension portion of the inner sleeve,
a tubular filter retainer is also inserted into the gas passage hole, and
a forward-facing surface of the filter retainer is in contact with the extension portion of the inner sleeve in a state in which the through-hole communicates with an internal space of the filter retainer.

8. The gas sensor according to claim 7, wherein
the gas passage filter is a sheet filter which covers an outer surface of the filter retainer,
the filter retainer has a collar portion which projects radially outward from a forward end of the filter retainer, and a forward-facing surface of the collar portion is in contact with the extension portion of the inner sleeve.

9. The gas sensor according to claim 4, wherein
the seal member has a gas passage hole extending therethrough in the axial direction, and
a water-repellent gas passage filter is inserted into the gas passage hole, the gas passage filter having a forward-facing surface in contact with the extension portion of the inner sleeve.

10. The gas sensor according to claim 5, wherein
the seal member has a gas passage hole extending therethrough in the axial direction, and
a water-repellent gas passage filter is inserted into the gas passage hole, the gas passage filter having a forward-facing surface in contact with the extension portion of the inner sleeve.

* * * * *